(12) United States Patent
Takahashi et al.

(10) Patent No.: US 10,251,536 B2
(45) Date of Patent: Apr. 9, 2019

(54) MEDICAL INSTRUMENT, MEDICAL SYSTEM, AND MODE TRANSITION METHOD FOR MEDICAL INSTRUMENTS

(71) Applicant: OLYMPUS CORPORATION, Tokyo (JP)

(72) Inventors: Keigo Takahashi, Tokyo (JP); Noriaki Yamanaka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 292 days.

(21) Appl. No.: 15/248,624

(22) Filed: Aug. 26, 2016

(65) Prior Publication Data
US 2016/0360950 A1 Dec. 15, 2016

Related U.S. Application Data

(63) Continuation of application No. PCT/JP2015/053576, filed on Feb. 10, 2015.

(30) Foreign Application Priority Data

Feb. 28, 2014 (JP) .................................. 2014-038278

(51) Int. Cl.
*A61B 1/00* (2006.01)
*A61B 1/005* (2006.01)
(Continued)

(52) U.S. Cl.
CPC .......... *A61B 1/0057* (2013.01); *A61B 1/0016* (2013.01); *A61B 1/00045* (2013.01);
(Continued)

(58) Field of Classification Search
CPC ... A61B 1/0057; A61B 1/0016; A61B 1/0052; A61B 1/00006; A61B 1/00045;
(Continued)

(56) References Cited

U.S. PATENT DOCUMENTS 8,915,841 B2 * 12/2014 Naito ................ A61B 1/00006
600/145
2001/0044570 A1 11/2001 Ouchi et al.
(Continued)

FOREIGN PATENT DOCUMENTS

JP H04-246322 A 9/1992
JP H08-206058 A 8/1996
(Continued)

OTHER PUBLICATIONS

International Search Report dated May 19, 2015 issued in PCT/JP2015/053576.
(Continued)

*Primary Examiner* — Timothy J Neal
(74) *Attorney, Agent, or Firm* — Scully, Scott, Murphy & Presser, P.C.

(57) ABSTRACT

The medical instrument a wire, a flexible sheath through which the wire is inserted, a wire driving unit for driving the wire, a passive unit that is put into operation as the wire is driven, a sheath pulling unit for pulling the sheath, a sheath lock unit for locking movement of the sheath, and a control unit for switching among a run-up mode in which the passive unit and the wire driving unit are still disconnected, a sheath free mode in which the sheath is not locked and so set free, a sheath slack adjustment mode in which a slack in the sheath is adjusted to lock the sheath in place and a master/slave mode in which the passive unit connected to the wire driving unit is put into a drivable state.

14 Claims, 15 Drawing Sheets

(51) Int. Cl.
*A61B 1/018* (2006.01)
*A61B 34/37* (2016.01)
*A61B 1/04* (2006.01)
*A61B 1/06* (2006.01)
*A61B 17/29* (2006.01)
*A61B 34/00* (2016.01)
*A61B 34/30* (2016.01)
*A61B 90/00* (2016.01)
*A61B 17/00* (2006.01)

(52) U.S. Cl.
CPC ........ *A61B 1/0052* (2013.01); *A61B 1/00133* (2013.01); *A61B 1/018* (2013.01); *A61B 1/04* (2013.01); *A61B 1/06* (2013.01); *A61B 34/37* (2016.02); *A61B 1/00006* (2013.01); *A61B 2017/00017* (2013.01); *A61B 2017/0034* (2013.01); *A61B 2017/00327* (2013.01); *A61B 2017/2905* (2013.01); *A61B 2034/301* (2016.02); *A61B 2034/715* (2016.02); *A61B 2090/061* (2016.02); *A61B 2090/064* (2016.02); *A61B 2090/0812* (2016.02)

(58) Field of Classification Search
CPC ..... A61B 1/04; A61B 1/00133; A61B 1/0018; A61B 1/06; A61B 34/37; A61B 2034/301
See application file for complete search history.

(56) References Cited

U.S. PATENT DOCUMENTS

| | | |
|---|---|---|
| 2008/0319260 A1 | 12/2008 | Murakami et al. |
| 2009/0192357 A1* | 7/2009 | Torii .................... A61B 1/0052 |
| | | 600/149 |
| 2011/0282153 A1 | 11/2011 | Ueki |
| 2012/0071752 A1 | 3/2012 | Sewell et al. |

FOREIGN PATENT DOCUMENTS

| | | |
|---|---|---|
| JP | 2001-258828 A | 9/2001 |
| JP | 2004-230201 A | 8/2004 |
| JP | 2007-185355 A | 7/2007 |
| JP | 2009-000500 A | 1/2009 |
| JP | 2009-106697 A | 5/2009 |
| JP | 4856289 B2 | 1/2012 |
| WO | 2014/084409 A1 | 6/2014 |

OTHER PUBLICATIONS

Partial Supplementary European Search Report dated Aug. 22, 2017 in European Patent Application No. 15 75 6018.6.

* cited by examiner

MEDICAL INSTRUMENT, MEDICAL SYSTEM, AND MODE TRANSITION METHOD FOR MEDICAL INSTRUMENTS

CROSS-REFERENCE TO RELATED APPLICATIONS

This application is a continuation claiming priority on the basis of Japan Patent Application No. 2014-038278 applied in Japan on Feb. 28, 2014 and based on PCT/JP2015/053576 filed on Feb. 10, 2015. The contents of both the PCT application and the Japan Application are incorporated herein by reference.

BACKGROUND OF THE INVENTION AND RELATED ART STATEMENT

The present invention relates to a medical instrument and a medical system that are each inserted through the body cavity of a patient for surgical operation to view, and apply treatments or the like to, the interior of the patient's body cavity as well as a mode transition method for the medical instrument.

There has been a medical instrument widely used in the art, in which an elongate insert unit is inserted into the body cavity of a patient and a wire or the like is used to haul the distal end of the insert unit to view, and apply treatments to, organs in the body cavity.

JP(A) 2009-106697 shows that a coil pipe is held in a given length for incorporation into an endoscope in a preferable state and improvements in the operability by an operating wire.

With the technology set forth in JP(A) 2009-106697, however, it is still impossible to take up slack in a sheath for the purpose of being well compatible with the shape of a flexible portion when there is a change in the shape of the flexible portion during treatment, because the sheath location has been fixed in place upon assembling.

SUMMARY OF INVENTION

The medical instrument according to one embodiment includes:
a wire,
a flexible sheath through which the wire is inserted,
a wire driving unit for driving the wire,
a passive unit that is put into operation as the wire is driven,
a sheath pulling unit for pulling the sheath,
a sheath lock unit for locking movement of the sheath, and
a control unit for switching among a run-up mode in which the passive unit and the wire driving unit are still disconnected, a sheath free mode in which the sheath is not locked and so set free, a sheath slack adjustment mode in which a slack in the sheath is adjusted to lock the sheath in place and a master/slave mode in which the passive unit connected to the wire driving unit is put into a drivable state.

According to one embodiment, a medical system provided that
the medical instrument is an endoscope including a viewing optical system, an imaging device and a lighting optical system,
and
the passive unit is defined by a distal-end portion of the endoscope to which one end of the wire is attached and a flexible portion through which the wire and the sheath are inserted, the medical system further includes:
an operating unit for driving the wire driving unit, to which the other end of the wire is attached, to put the distal-end portion and the flexible portion into operation,
a display unit for displaying an image acquired through the endoscope, and
a system control unit for putting the operating unit into operation thereby controlling the endoscope and permitting the image acquired through the endoscope to be displayed on the display unit.

One embodiment provides a mode transition method for a medical apparatus which includes:
a wire,
a flexible sheath through which the wire is inserted,
a wire driving unit for driving the wire,
a passive unit that is put into operation as the wire is driven,
a sheath pulling unit for pulling the sheath, and
a sheath lock unit for locking movement of the sheath,
the method includes
a run-up mode in which the passive unit and the wire driving unit are still disconnected,
a sheath free mode in which the sheath is not locked and so set free,
a sheath slack adjustment mode in which a slack in the sheath is adjusted to lock the sheath in place
and
a master/slave mode in which the passive unit connected to the wire driving unit is put into an enabling state,
the method includes the step of:
transiting to the sheath free mode, when the passive unit is connected to the wire driving unit in the run-up mode,
transiting to the sheath slack adjustment mode, when completion of connection of the passive unit to the wire driving unit is verified in the sheath free mode,
and
transiting to the master/slave mode, when the sheath has a sheath tension within a predetermined range and is locked in the sheath slack adjustment mode.

DESCRIPTION OF EMBODIMENTS

Some embodiments are now explained.

Figure 1:
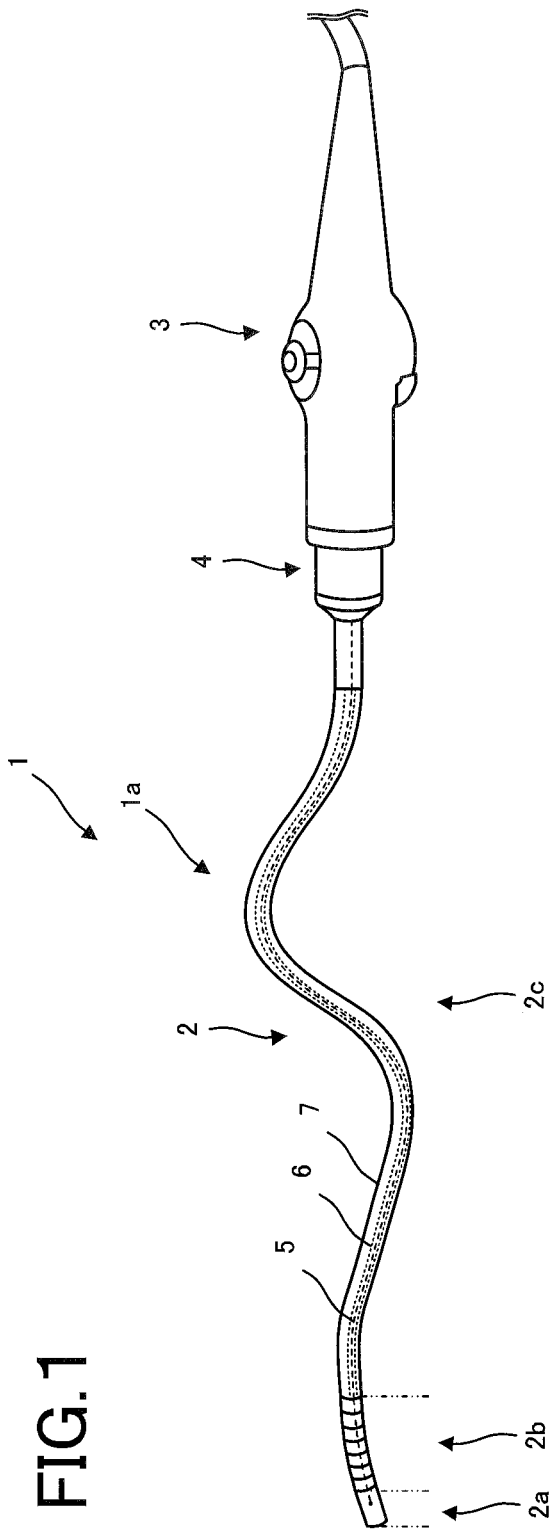
FIG. 1 is a schematic view of the medical instrument according to one embodiment.

FIG. 1 is a schematic view of one example of the medical instrument 1 according to one embodiment.

One example of the medical instrument 1 according to the embodiment described herein includes an endoscope 1a including at least an insert unit 2, an operating unit 3, a wire driving unit 4, a wire 5 and a sheath 6. The medical instrument 1 has the insert unit 2 on a distal-end side and the operating unit 3 on a proximal-end side. Inserted through the body cavity, the insert unit 2 includes, in order from the distal-end side, a distal-end portion 2a, a curving portion 2b and a flexible portion 2c. The flexible portion 2c is covered on its outer circumference with an outer cover 7. Note here that the curving portion 2b may be dispensed with or, alternatively, a joint portion may be used in place of the curving portion 2b. Referring to the operating unit 3, the wire 5 is driven by the wire driving unit 4 for operation of the curving state of the curving portion 2b and the orientation of the distal-end portion 2a. The operating unit 3 and wire driving unit 4 are connected to a power source, a controller or the like (not shown) by way of cables. The insert unit 2 and driving unit 4 are detachable from each other or, alternatively, the wire driving unit 4 may be built in the operating unit 3.

Figure 2:
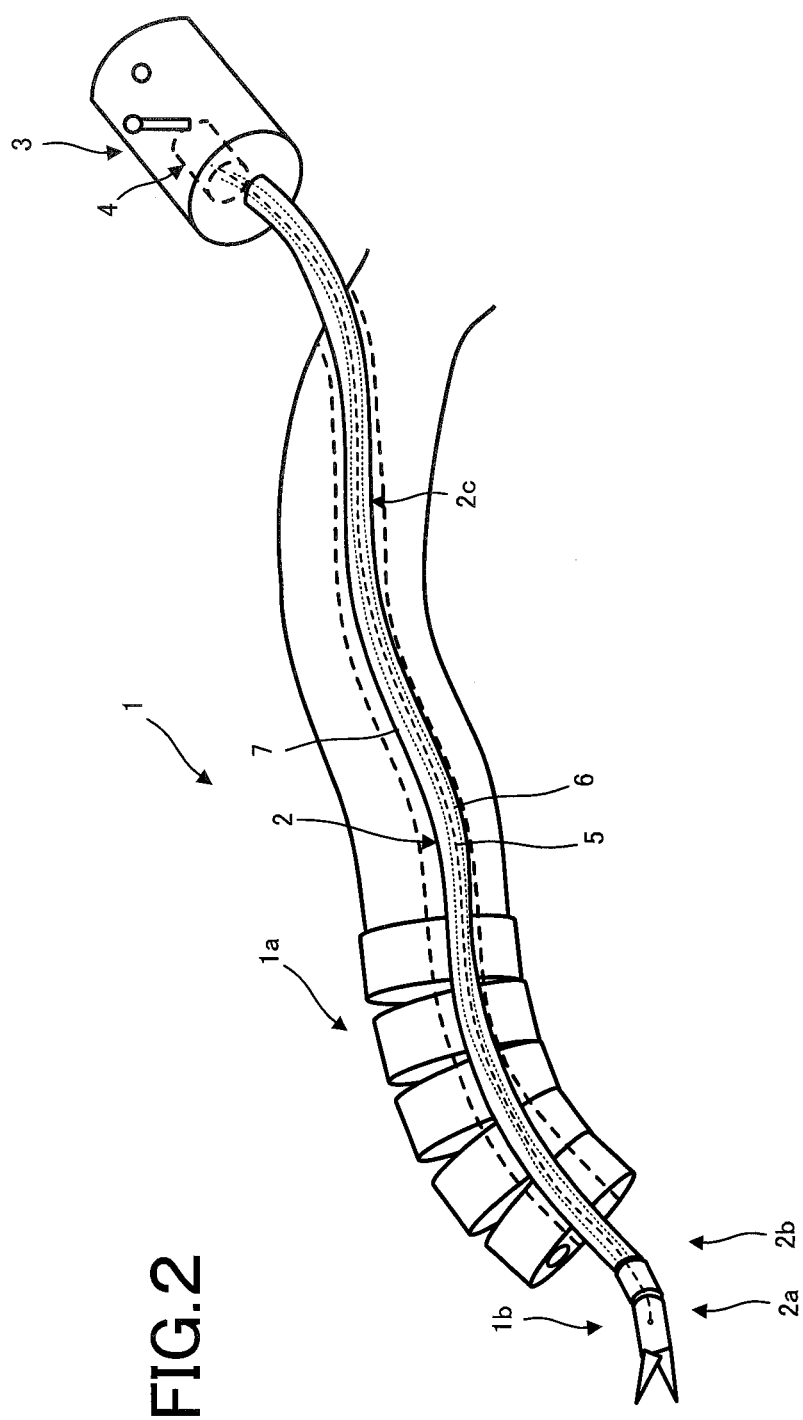
FIG. 2 is a schematic view of another example of the medical instrument according to the embodiment.

FIG. 2 is a schematic view of another example of the medical instrument 1 according to the embodiment described herein.

Another example of the medical instrument 1 according to the embodiment described herein includes a treatment tool 1b including at least an insert unit 2, an operating unit 3, a wire driving unit 4, a wire 5 and a sheath 6, and is used while inserted inside the endoscope 1a. The medical instrument 1 has the insert unit 2 on a distal-end side and the operating unit 3 on a proximal-end side. Inserted together with the endoscope through the body cavity, the insert unit 2 includes, in order from the distal-end side, a distal-end portion 2a, a curving portion 2b and a flexible portion 2c. The flexible portion 2c is covered on its outer circumference with an outer cover 7. Note here that the curving portion 2b may be dispensed with or, alternatively, a joint portion may be used in place of the curving portion 2b. Referring to the operating unit 3, the wire 5 is driven by the wire driving unit 4 for operation of the curving state of the curving portion 2b and the orientation of the distal-end portion 2a. Note here that a treatment fool such as a pair of forceps may be put by the operating unit 3 into operation. The operating unit 3 and wire driving unit 4 are connected to a power source, a controller or the like (not shown) by way of cables. The insert unit 2 and wire driving unit 4 are detachable from each other or, alternatively, the wire driving unit 4 may be built in the operating unit 3.

In the examples shown in FIGS. 1 and 2, one end of the wire 5 is attached to the distal-end portion 2b and the other is coupled to the wire driving unit 4. The sheath 6 is mounted inside the outer cover 7, and there is the wire 5 inserted inside the sheath 6.

Figure 3A:
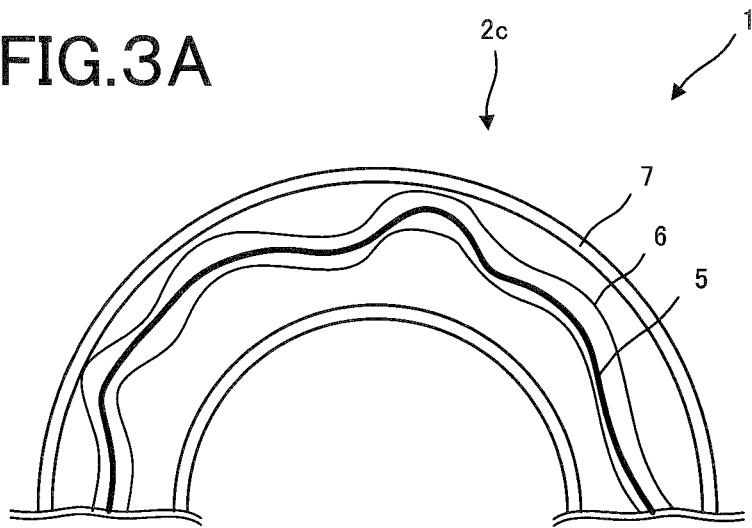
FIGS. 3A and 3B are a schematic view of one example of the flexible portion of the medical instrument according to one embodiment.
Figure 3B:
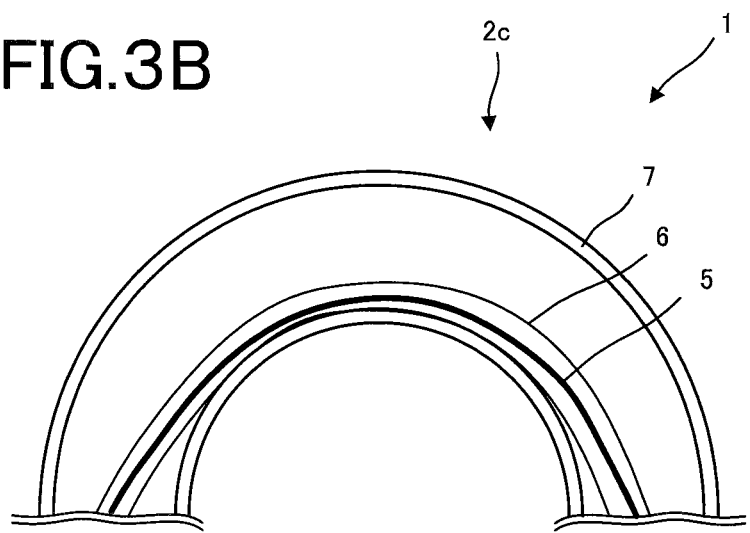

FIGS. 3A and 3B are a schematic view of one example of the flexible portion 2c of the medical instrument 1 according to the embodiment described herein: FIG. 3A shows that the sheath 6 and wire 5 are slacking with respect to the outer cover 7 over the flexible portion 2c and FIG. 3B shows that the sheath 6 and wire 5 are pulled from the state of FIG. 3A.

The flexible portion 2c includes the outer cover 7, the sheath 6 inserted inside the outer cover 7 and the wire 5 inserted inside the sheath 6. The flexible portion 2c takes on various shapes depending on conditions under which the medical instrument 1 is used.

Referring to the medical instrument 1 according to the embodiment described herein, when the flexible portion 2c curves and the sheath 6 slacks as shown in FIG. 3A, the sheath 6 is pulled as shown in FIG. 3B after the shape of the flexible portion 2c is fixed so that the slack is removed and the sheath 6 is fixed in such a way as to route through the shortest path within the outer cover 7. Then, the wire 5 is driven in the state shown in FIG. 3B, leading not only to an increased resistance to compression and a decreased friction, but also to no or little change in performance characteristics depending on shape changes, which results in excellent responsiveness and ease of control.

The sheath lock mechanism 10 according to the embodiment described herein that is used with the medical instrument 1 shown in FIG. 1 or 2 is now explained.

Figure 4A:
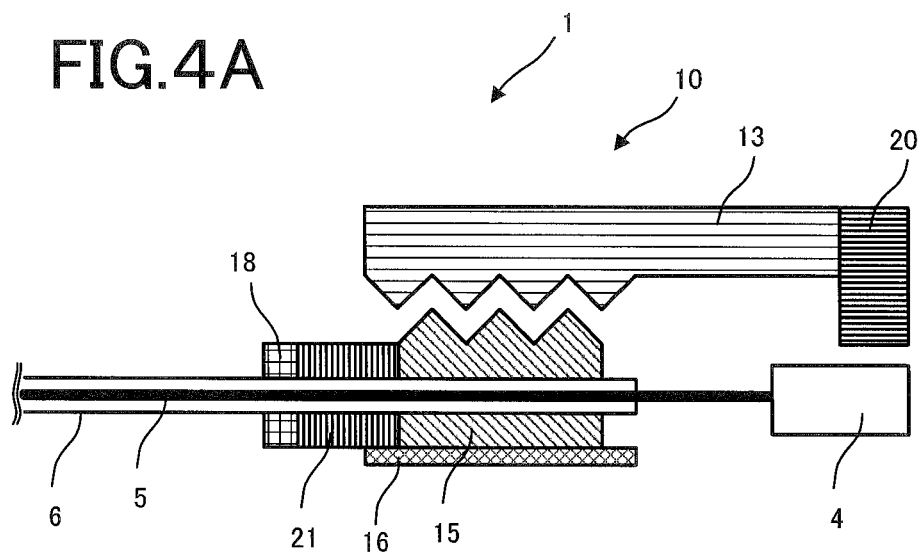
FIGS. 4A and 4B are a schematic view of the sheath lock mechanism for the medical instrument according to one embodiment.
Figure 4B:
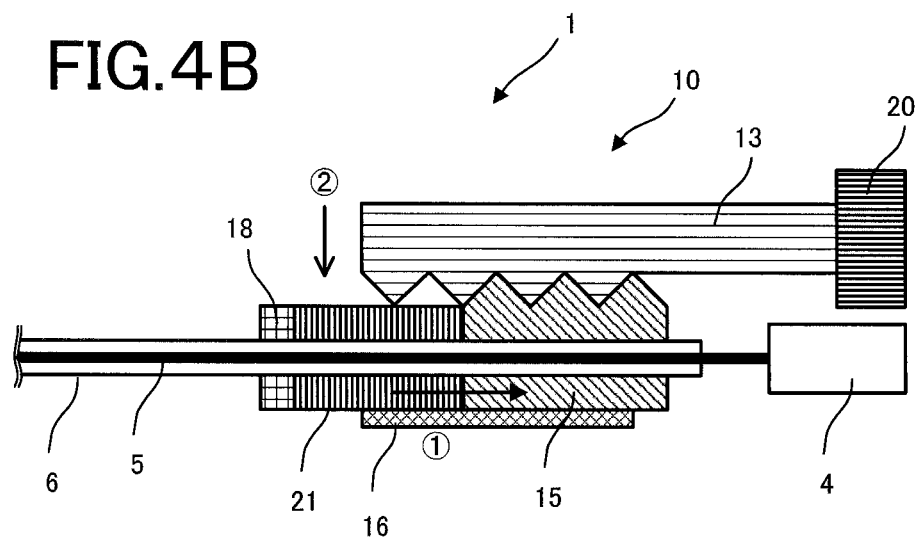

FIGS. 4A and 4B are a schematic view of the sheath lock mechanism 10 for the medical instrument 1 according to the embodiment described herein: FIG. 4A is a schematic view of the sheath lock mechanism 10 according to the embodiment before movement and FIG. 4B is a schematic view of the sheath lock mechanism 10 according to the embodiment after movement.

The sheath lock mechanism 10 for the medical instrument 1 according to the embodiment described herein includes a sheath lock member 13, a wire driving unit 4, a sheath support member 15, a sheath support member guide 16, a through-the-sheath unit 18, sheath lock driving unit 20 and a sheath pulling driving unit 21. Note here that the sheath lock mechanism 10 may be located in the operating unit 3 shown in FIG. 1, and that the sheath support member guide 16 and through-the-sheath unit 18 may be fixed to the outer cover 7 over the flexible unit 2c shown in FIGS. 3A and 3B.

As shown in FIG. 4A, the sheath lock driving unit 20 such an actuator is driven to move the sheath lock member 13 of the sheath lock mechanism 10 in a direction of coming into engagement with, or spacing away from, the sheath support member 15. The sheath support member 15 is previously fixed to the sheath 6, and mounted between the through-the-sheath unit 18 and the sheath support member 15 in such a way as to extend or contract in a direction of pulling or retracting the sheath 6 by means of the sheath pulling driving unit 21 such as an actuator. The wire 5 is attached to the wire driving unit 4.

The sheath lock mechanism 10 is activated by a switch (not shown) or the like. First, the sheath support member 15 is moved by the sheath pulling driving unit 21 in a direction of pulling the sheath 6 to reduce the slack in the sheath 6. Then, the sheath lock driving unit 20 is driven to bring the sheath lock member 13 in engagement with the sheath support member 15, as shown in FIG. 4B. Thus, the sheath 6 maintains shape in a less slacking state. Note here that whether or not the sheath is locked may be determined depending on the driving status of the sheath lock driving unit 20 or, alternatively, by use of a lock detection unit (not shown) to detect movement of the sheath lock member 13.

Such sheath lock mechanism 10 according to the embodiment described herein ensures that the sheath 6 can be pulled and fixed in place under constant tension thereby placing the sheath 6 in a slack-free shape.

Control of the medical instrument 1 according to the embodiment described herein is now explained.

Figure 5:
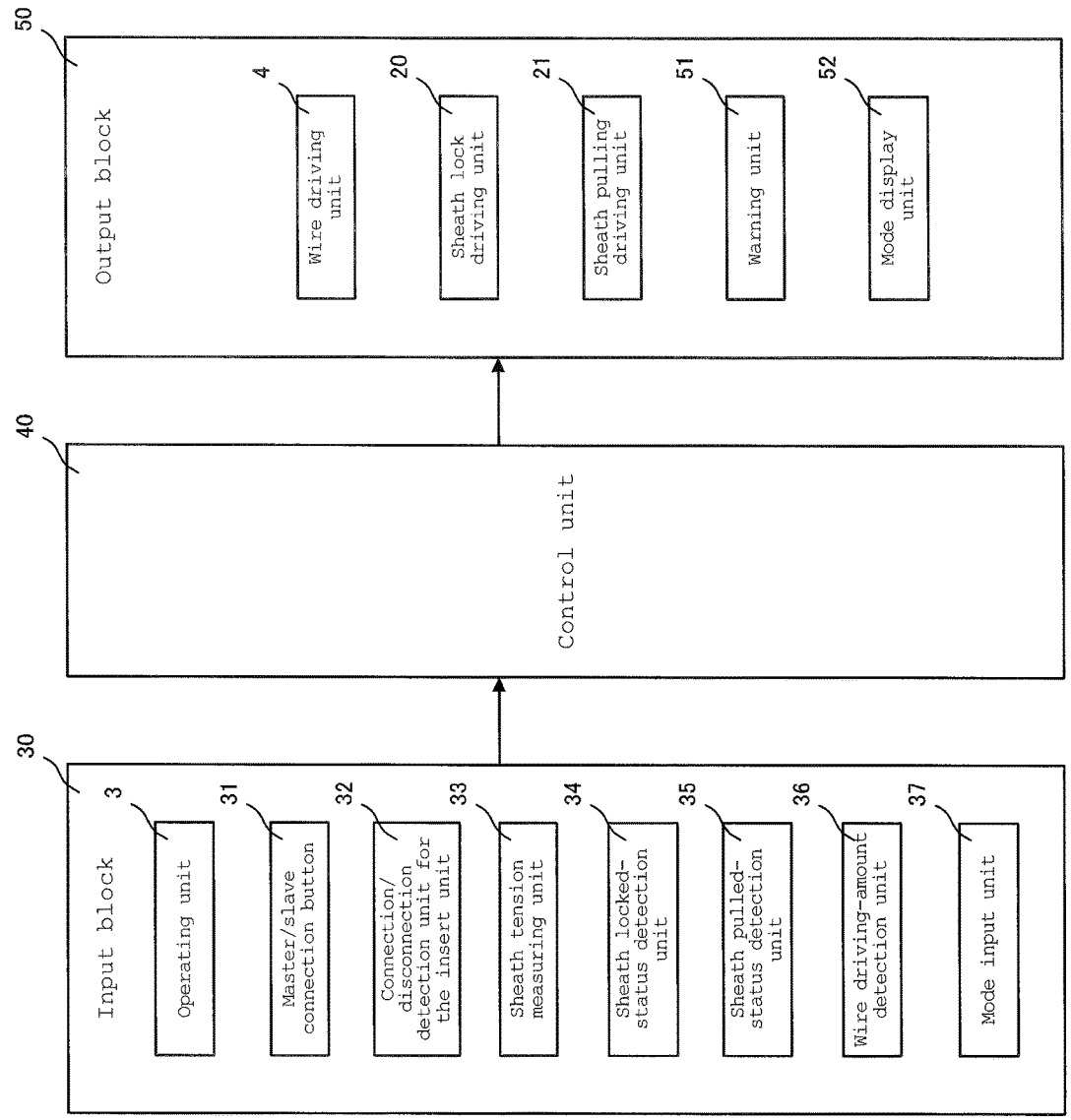
FIG. 5 is illustrative of a control block for the medical instrument according to one embodiment.

FIG. 5 is indicative of a control block for the medical instrument 1 according to the embodiment described herein.

The medical instrument 1 according to the embodiment described herein includes such a control unit as shown in FIGS. 4A and 4B. However, it is to be noted that all units included in the input 30 and the output block 50 are not necessarily used; at least some units may be used depending on the structural requirements.

Referring to an input block or unit 30, the distal-end portion 2a, curving portion 2b, etc. are put by the operating unit 3 into operation, as already described. A master/slave connection button 31 is defined by a switch by which a surgeon gives an instruction as to master/slave connection. In the embodiment described herein, that switch gives an instruction as to connection of the insert unit 2 to the wire driving unit 4. The connection/disconnection detection unit 32 is defined by a sensor for detecting the connection of the insert unit 2 to the wire driving unit 4. The sheath tension measuring unit 33 is defined by a sensor for detecting the tension of the sheath 6, and the sheath locked-status detection unit 34 is defined by a sensor for detecting the status of the sheath 6. In the embodiment described herein, the sheath locked-status detection unit 34 is specifically a sensor for detecting whether or not the sheath support member 15 is locked by the sheath lock driving unit 20. A sheath pulled-status detection unit 35 is defined by a sensor for detecting a driving status of the sheath pulling driving unit 21 for pulling the sheath 6. Status parameters to be detected may be a driving amount for pulling the sheath 6, a time for which the sheath 6 is pulled, and so on. A wire driving-amount detection unit 36 is defined by a sensor for detecting the driving amount of the wire driving unit 4. A mode input unit 37 is provided to enter a mode by means of a selection button, an icon or the like. Note here that the connection/disconnection detection unit 32, sheath locked-status detection unit 34 and wire driving-amount detection unit 36 may be dispensed with.

The output block 50 includes the wire driving unit 4, sheath lock member driving unit 20 and sheath pulling driving unit 21 as well as a warning unit 51 and a mode display unit 52. The warning unit 51 notifies those around one of errors, if any, by way of a screen display, a buzzer, etc. The mode display unit 52 produces a screen display of the current mode in operation.

The modes controlled by the control unit 40 in the medical instrument 1 according to the embodiment described herein are now explained.

Figure 6:
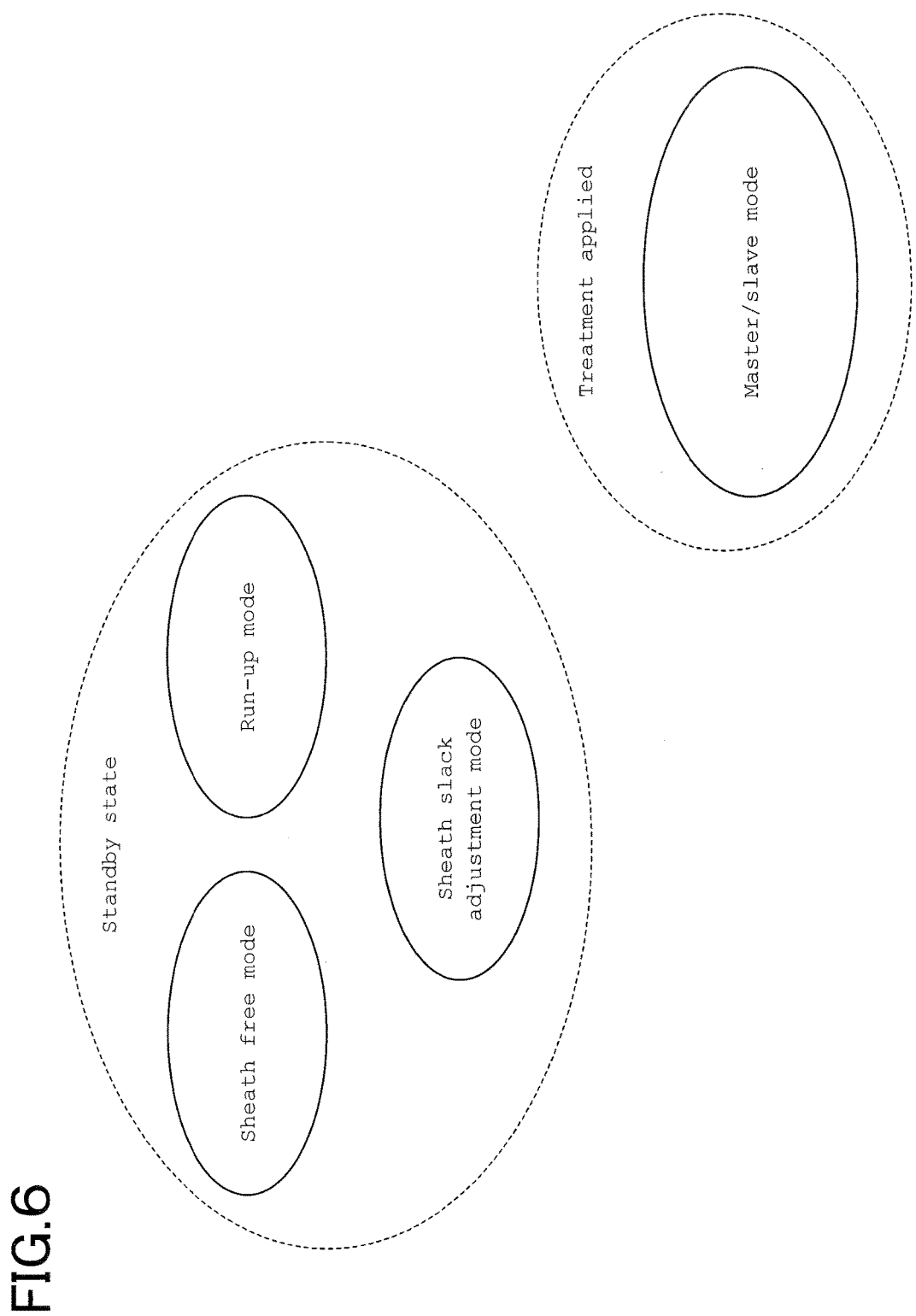
FIG. 6 is illustrative of the control mode of the control unit in the medical instrument according to one embodiment.

FIG. 6 is indicatives of the modes controlled by the control unit 40 in the medical instrument 1 according to the embodiment described herein are now explained.

In status terms, the medical instrument 1 according to the embodiment described herein is generally available in a standby status and a treatment status. In the standby status, an instruction value entered from the input block 30 shown in FIG. 5 is neglected, and in the treatment status, the insert unit 2 shown in FIG. 1 or 2 is put into operation.

The standby status includes a run-up mode, a sheath free mode, and a sheath slack adjustment mode. In the run-up mode, the master/slave connection is on standby, and the initialization of the system and motor already gets done. In the sheath free mode, the sheath 6 is not locked and so set free as shown in FIG. 4A, and in the sheath slack adjustment mode, the sheath 6 is locked to adjust slack as shown in FIG. 4B.

The treatment status includes a master/slave mode. In the master/slave mode, the insert unit 2 connected to the wire driving unit 4 is put into operation and the amount of slack in the sheath 6 is already adjusted.

According to the medical instrument 1 disclosed herein, it is thus possible to control the status of the sheath 6 unerringly in association with the status of the apparatus.

The control flow for each mode of the medical instrument 1 according to the embodiment described herein is now explained.

Figure 7:
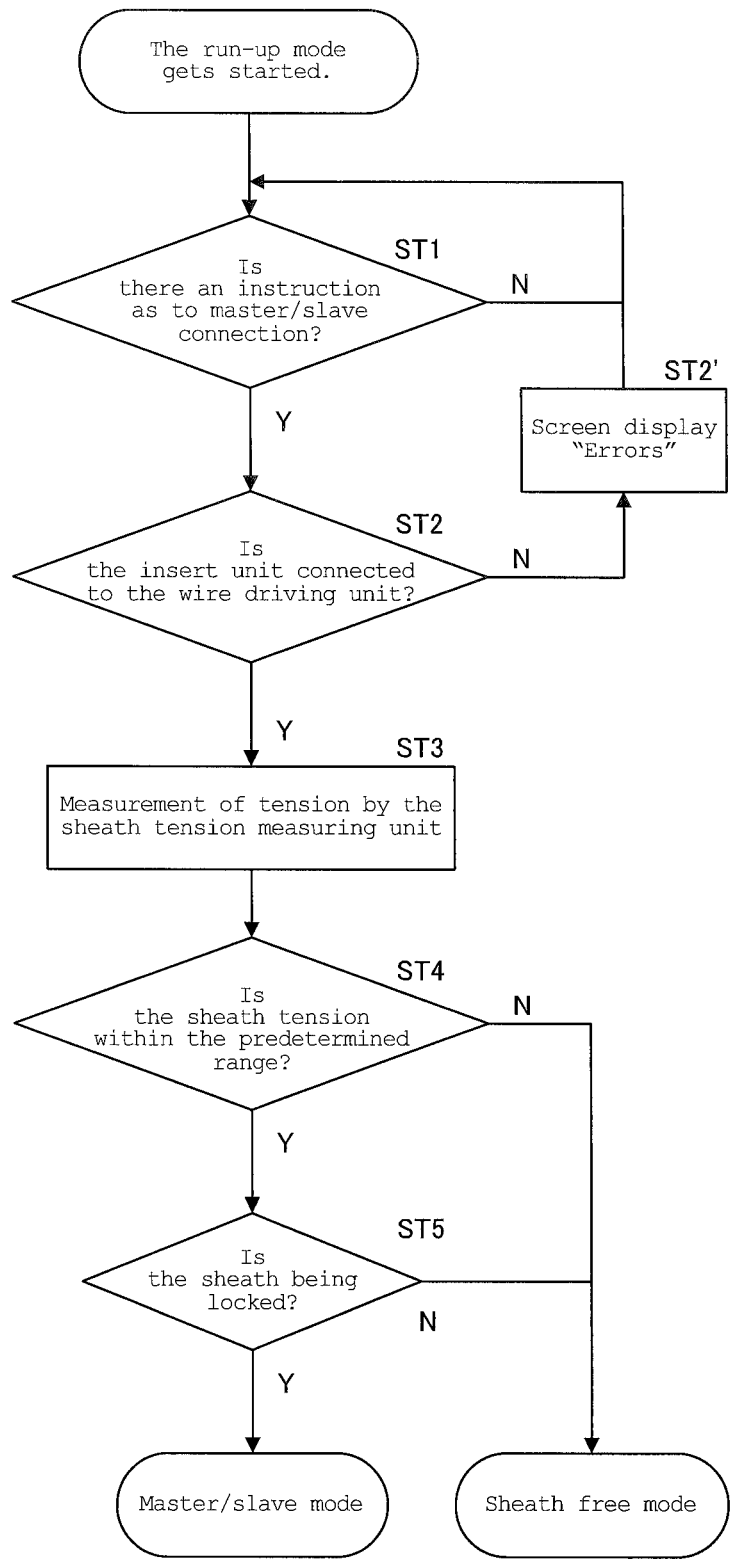
FIG. 7 is a control flowchart for the run-up mode of the medical instrument according to one embodiment.

FIG. 7 is indicative of a control flow in the run-up mode of the medical instrument 1 according the embodiment described herein.

In the run-up mode of the medical instrument 1 according to the embodiment described herein, it is determined in Step 1 whether or not there is an instruction entered from the master/slave connection button 31 as to the master/slave connection (ST1). If there is no instruction as to the master/slave connection, the processing then goes back to Step 1.

In Step 1, if there is an instruction as to the master/slave connection, the processing then goes to Step 2 in which it is determined by the connection/disconnection detection unit 32 whether or not the insert unit 2 is connected to the wire driving unit 4 (ST2). Note here that this step may be dispensed with when the connection/disconnection detection unit 32 is not provided.

In Step 2, if the insert unit 2 is determined as being still disconnected from the wire driving unit 4, the processing goes to Step 2' in which the warning unit (not shown) or the like produces a screen display "Error" (ST2'), and goes back to Step 1.

In Step 2, if the insert unit 2 is determined as being connected to the wire driving unit 4, the processing then goes to Step 3 in which the tension of the sheath 6 is measured by the sheath tension measuring unit 33 (ST3).

Then, the processing goes to Step 4 in which it is determined whether or not the thus measured tension of the sheath 6 has a value within a predetermined range (ST4). In Step 4, if the measured tension of the sheath 6 does not have a value within the predetermined range, the processing then goes to the sheath free mode.

In Step 4, if the measured tension of the sheath 6 has a value within the predetermined range, the processing then goes to Step 5 in which it is determined by the sheath locked-status detection unit 34 whether or the sheath 6 is being locked (ST5). Note here that this step may be dispensed with when the sheath locked-status detection unit 34 is not provided.

In Step 5, if the sheath 6 is determined by the sheath locked-status detection unit 34 as being locked, the processing then goes to the master/slave mode. In Step 5, if the sheath 6 is determined by the sheath locked-status detection unit 34 as being not locked, the processing then goes to the sheath free mode.

Figure 8:
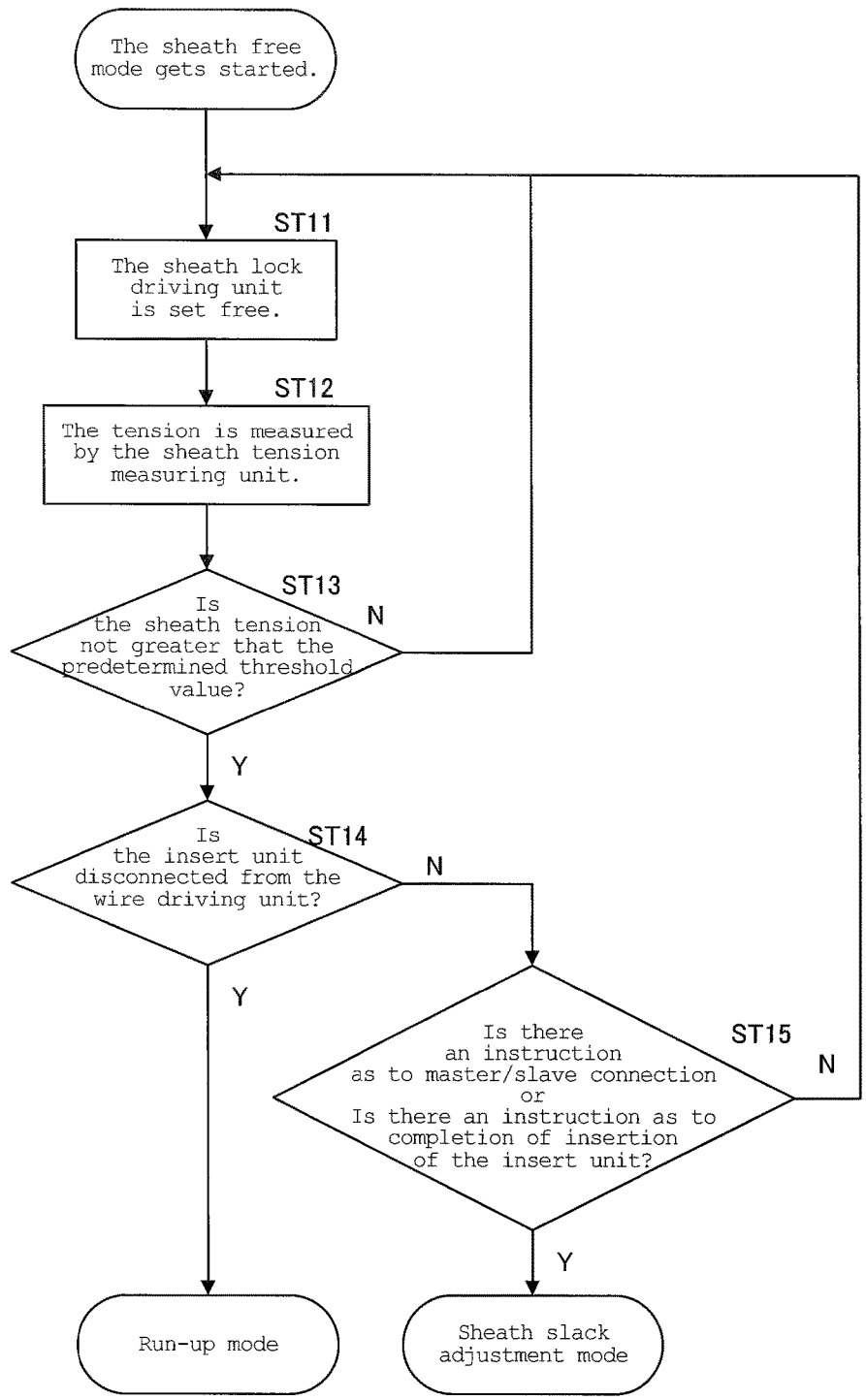
FIG. 8 is a control flowchart for the sheath free mode for the medical instrument according to one embodiment.

FIG. 8 is indicative of the control flow in the sheath free mode of the medical instrument 1 according to the embodiment described herein.

Referring to the sheath free mode of the medical instrument 1 according to the embodiment described herein, the sheath lock driving unit 20 is set free in Step 11 (ST11). In other words, the sheath lock member 13 shown in FIGS. 3A and 3B is spaced away from the sheath support member 15.

Then, the processing goes to Step 12 in which the tension of the sheath 6 is measured by the sheath tension measuring unit 33 (ST12).

Then, the processing goes to Step 13 in which it is determined whether or not the thus measured tension of the sheath 6 is less than a predetermined threshold value (ST13). In Step 13, if the measured tension of the sheath 6 is not less than the predetermined threshold value, the processing then goes back to Step 11.

In Step 13, if the measured tension of the sheath 6 is less than the predetermined threshold value, the processing then goes to Step 14 in which it is determined whether or not the insert unit 2 is disconnected from the wire driving unit 4 by the connection/disconnection detection unit 32 (ST14).

In Step 14, if the insert unit 2 is determined by the connection/disconnection detection unit 32 as being disconnected from the wire driving unit 4, the processing then goes to the run-up mode.

In Step 14, if the insert unit 2 is determined by the connection/disconnection detection unit 32 as being not yet disconnected from the wire driving unit 4, the processing then goes to Step 15 in which it is determined whether or not there is an instruction entered from the master/slave connection button 31 as to the master/slave connection (ST15).

In Step 15, if there is no instruction entered as to the master/slave connection, the processing then goes back to Step 11. In Step 15, if there is an instruction entered as to the master/slave connection, the processing then goes to the sheath slack adjustment mode.

In the sheath free mode of the medical instrument 1 according to the embodiment described herein, it is thus possible to gain unerring control of the medical instrument in such a way as not to apply treatment when the insert unit 2 is still disconnected from the wire driving unit 4.

Figure 9:
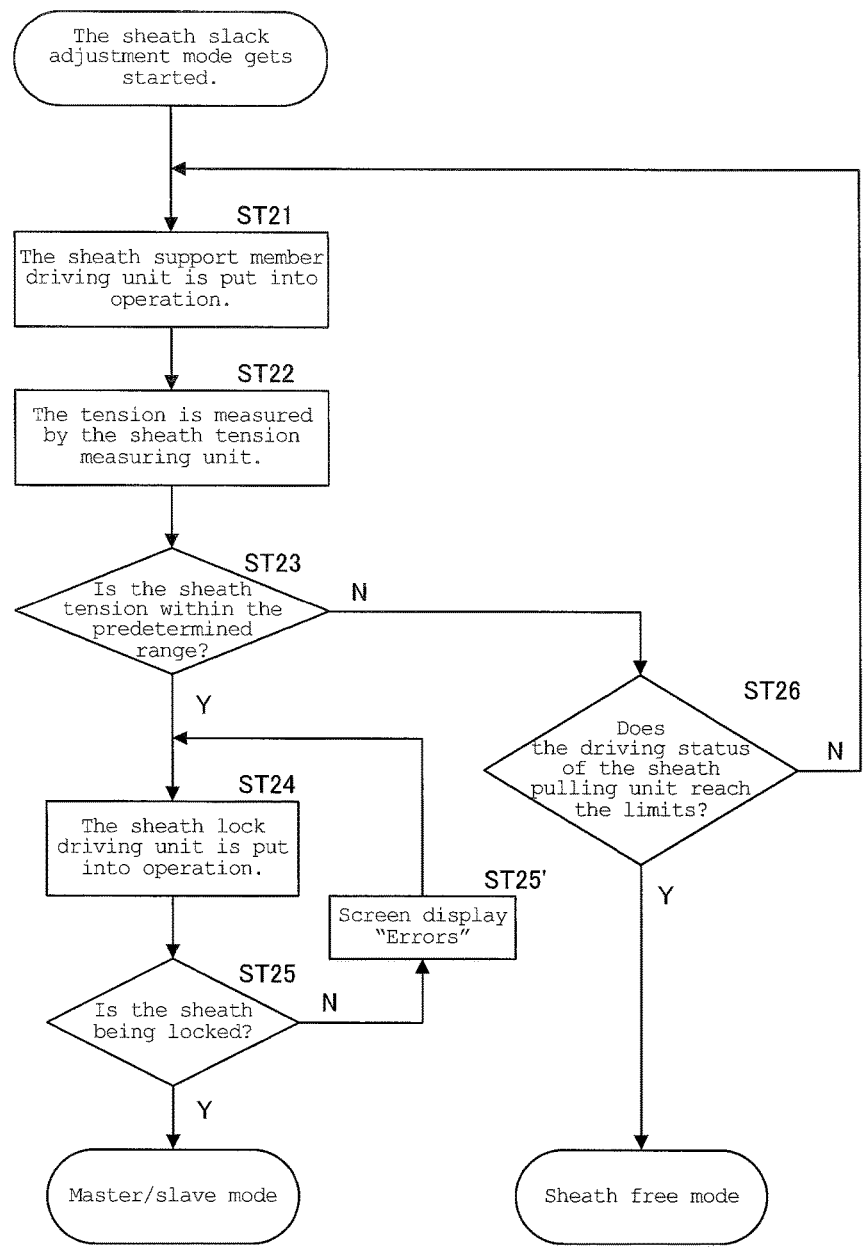
FIG. 9 is a control flowchart for the sheath slack adjustment mode of the medical instrument according to one embodiment.

FIG. 9 is indicative of a control flow in the sheath slack adjustment mode of the medical instrument 1 according to the embodiment described herein.

Referring to the sheath slack adjustment mode of the medical instrument 1 according to the embodiment described herein, the sheath pulling driving unit 21 is first actuated in Step 21 (ST21).

Then, the processing goes to Step 22 in which the tension of the sheath 6 is measured by the sheath tension measuring unit 33 (ST22).

Then, the processing goes to Step 23 in which it is determined whether or not the thus measured tension of the sheath 6 has a value within a predetermined range (ST23). In Step 23, if the measured tension of the sheath 6 has a value within the predetermined range, the processing then goes to Step 24 in which the sheath lock driving unit 20 is actuated (ST24).

Then, the processing goes to Step 25 in which it is determined by the sheath locked-status detection unit 34 whether or not the sheath 6 is being locked (ST25). Note here that this step may be dispensed with when the sheath lock status detection unit 34 is not provided.

In Step 25, if the sheath 6 is determined by the sheath locked-status detection unit 34 as being locked, the processing then goes to the master/slave mode. In Step 25, if the sheath 6 is determined by the sheath locked-status detection unit 34 as being not locked, the processing then goes to Step 25' in which the warning unit (not shown) or the like produces a screen display "Error" (ST25') and goes back to Step 24. Note here that Step 25' may go to the run-up mode for compensation of errors.

In Step 23, if the measured tension of the sheath 6 does not have a value within the predetermined range, the processing then goes to Step 26 in which it is determined whether or not the sheath-pulled status detected by the sheath pulled-status detection unit 35 reaches the limits (ST26). The "limits to the sheath-pulled status" means that the predetermined driving amount is exceeded, the predetermined time is exceeded, or the like.

In Step 26, if the sheath pulled-status is determined as reaching the limits, the processing then goes to the sheath free mode. Note here that if the sheath pulled-status is determined in Step 26 as reaching the limits, Step 26 may go to the run-up mode for compensation of errors.

In Step 26, if the sheath pulled-status is determined as not reaching the limits, the processing then goes back to Step 21.

In the sheath slack adjustment mode of the medical instrument 1 according to the embodiment described herein, it is thus possible to make unerring sheath adjustment in association with the status of the sheath 6.

Figure 10:
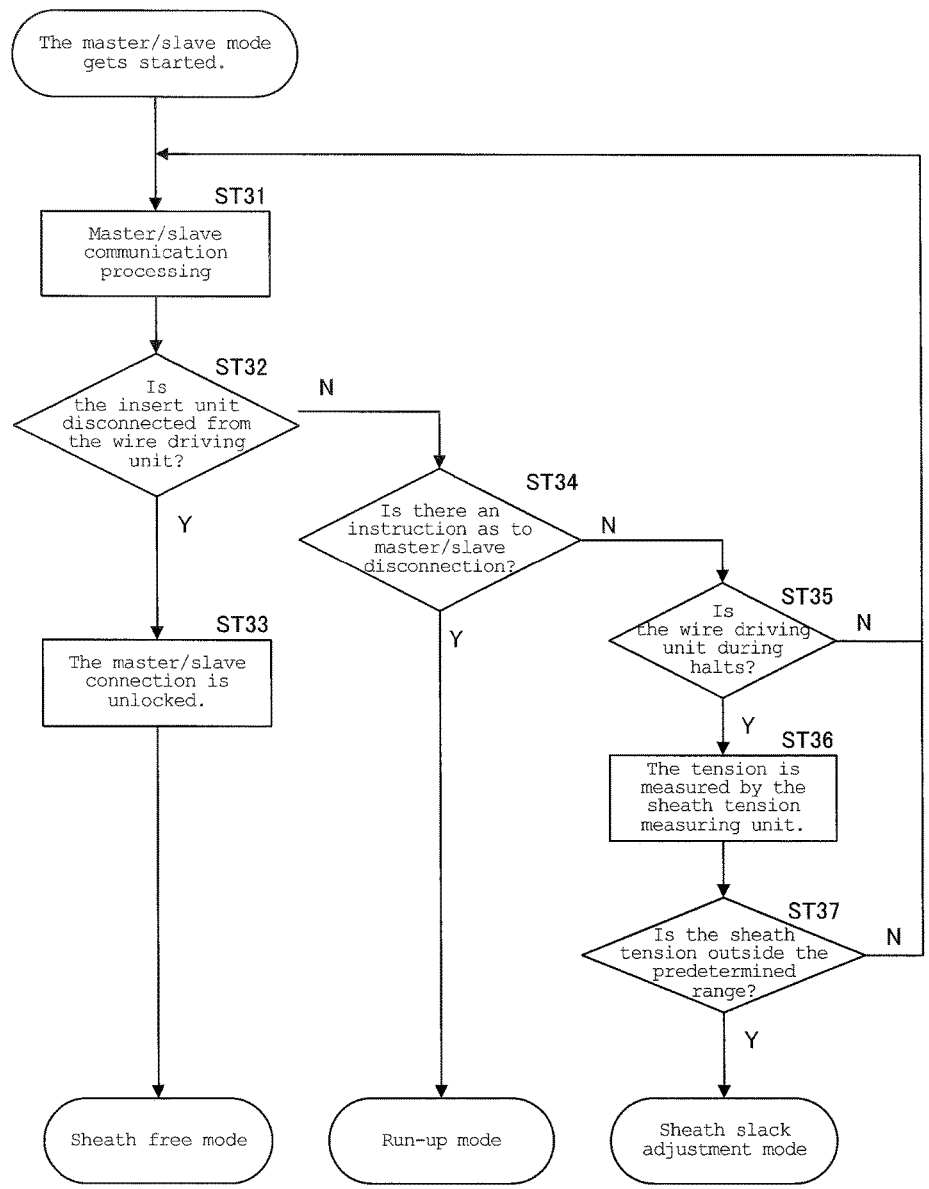
FIG. 10 is a control flowchart for the master/slave mode of the medical instrument according to one embodiment.

FIG. 10 is indicative of a control flow for the master/slave mode of the medical instrument 1 according to the embodiment described herein.

In the master/slave mode of the medical instrument 1 according to the embodiment described herein, master/slave communication processing is implemented in Step 31 (ST31).

Then, the processing goes to Step 32 in which it is detected by the connection/disconnection detection unit 32 whether or not the insert unit 2 is still disconnected from the wire driving unit 4 (ST32).

In Step 32, if the insert unit 2 is determined by the connection/disconnection detection unit 32 as being still disconnected from the wire driving unit 4, the processing then goes to Step 33 in which the master/slave connection is set free (ST33), and then goes to the sheath free mode. Note here that it may go to the run-up mode instead.

In Step 32, if the insert unit 2 is determined by the connection/disconnection detection unit 32 as being not yet disconnected from the wire driving unit 4, the processing then goes to Step 34 in which it is determined whether or not there is an instruction entered from the master/slave connection button 31 as to setting the master/slave connection free (ST34). In Step 34, if there is an instruction as to setting the master/slave connection free, the processing then goes to the run-up mode.

In Step 34, if there is not an instruction as to setting the master/slave connection free, the processing then goes to Step 35 in which it is determined whether or not the wire driving unit 4 is during halts (ST35). In Step 35, if the wire driving unit 4 is not during halts, the processing then goes back to Step 31.

In Step 35, if the wire driving unit 4 is during halts, the processing then goes to Step 36 in which the tension of the sheath 6 is measured by the sheath tension measuring unit 33 (ST36).

Then, the processing goes to Step 37 in which it is determined whether or not the thus measured tension of the sheath 6 has a value outside the predetermined range (ST37).

In Step 37, if the measured tension of the sheath 6 does not have a value outside the predetermined range, the processing then goes back to Step 31. In Step 37, if the measured tension of the sheath 6 has a value outside the predetermined range, the processing then goes to the sheath slack adjustment mode.

In the master/slave mode of the medical instrument 1 according to the embodiment described herein, it is thus possible to adjust the slack in the sheath 6 when the status of the sheath 6 is not unerring, thereby putting the insert unit 2 into operation in an unerring sheath 6 status.

Control processing from the activation to deactivation of the medical instrument 1 according to the embodiment described herein is now explained as an example.

Figure 11:
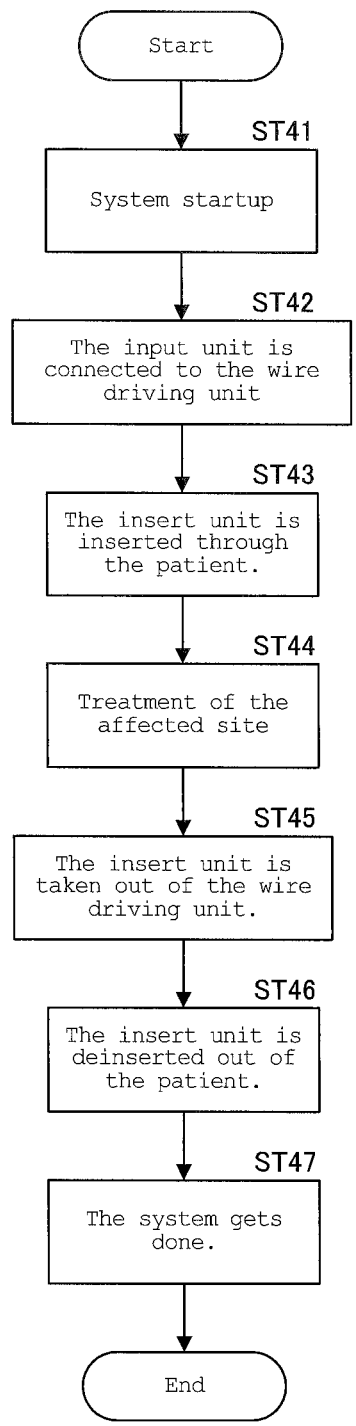
FIG. 11 is a control flowchart from the activation to the deactivation of the medical instrument according to one embodiment.

FIG. 11 is indicative of a control flow from the activation to deactivation of the medical instrument 1 according to the embodiment described herein.

First of all, reference is made to control processing from the activation to deactivation of the medical instrument 1. In an example here, the apparatus is activated or actuated in Step 41 (ST41). Then, the processing goes to Step 42 in which the insert unit 2 is connected to the wire driving unit 4 (ST42). Then, the processing goes to Step 43 in which a part of the insert unit 2 is inserted through a patient (ST43). Then, the processing goes to Step 44 in which an affected site is treated (ST44). Then, the processing goes to Step 45 in which the insert unit 2 is disconnected from the wire driving unit 4 (ST45), and then goes to Step 46 in which a part of the insert unit 2 is pulled out of the patient (ST46). Finally, the processing goes to Step 47 in which the control gets done (ST47).

Reference is then made to an example wherein control of the medical instrument 1 corresponds to each mode.

Figure 12:
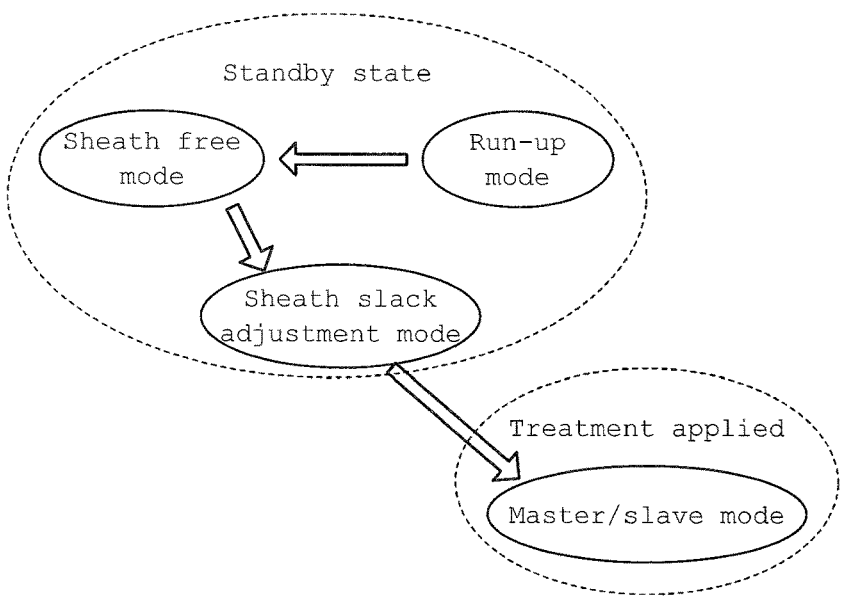
FIG. 12 is illustrative of one example of the mode transitions from the insertion of an insert unit of the medical instrument according to one embodiment to the treatment of an affected site.

FIG. 12 is illustrative of one example of the mode transition from the insertion of a part of the insert unit of the medical instrument according to the embodiment described herein to the treatment of an affected site.

In Steps 42 and 43 shown in FIG. 11, there is such mode transition as shown typically in FIG. 12. First in the run-up mode, the connection of the insert unit 2 to the wire driving unit 4 is detected after which the processing goes to the sheath free mode in which the completion of the master/slave connection or the insertion of a part of the insert unit 2 is notified to a surgeon or the like by way of a switch such as a button or a completion-of-insertion sensor, etc., and makes a transition to the sheath slack adjustment mode in which the tension of the sheath is adjusted within a given range. Then, the processing goes to the master/slave mode.

Figure 13:
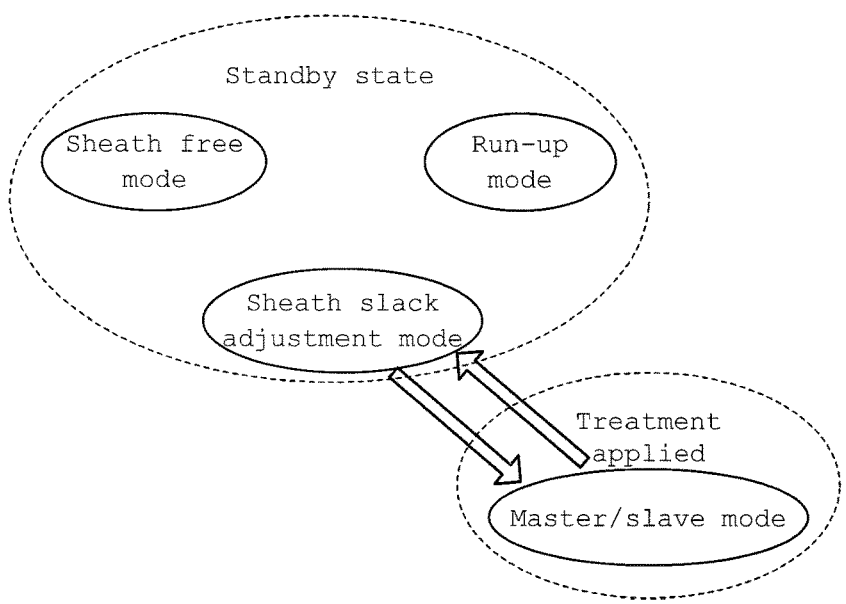
FIG. 13 is indicative of mode transitions to the treatment of an affected site by the medical instrument one embodiment.

FIG. 13 is indicative of the mode transition for the treatment of an affected site by the medical instrument according to the embodiment described herein.

In Step 44 shown in FIG. 11, there is such mode transition as shown typically in FIG. 13. In the master/slave mode, if the sheath tension has a value outside a given range, the processing goes to the sheath slack adjustment mode in which the sheath tension is adjusted to within the given range, followed by making a transition to the master/slave mode. Note here that the transition from the master/slave mode to the sheath slack adjustment mode occurs not only when the sheath tension has a value outside the given range, but also when the adjustment button is pressed down, there is a change in the bodily position of the patient, a change in the shape of a part of the insert unit 2 is detected out of an endoscopic image or the like.

Figure 14:
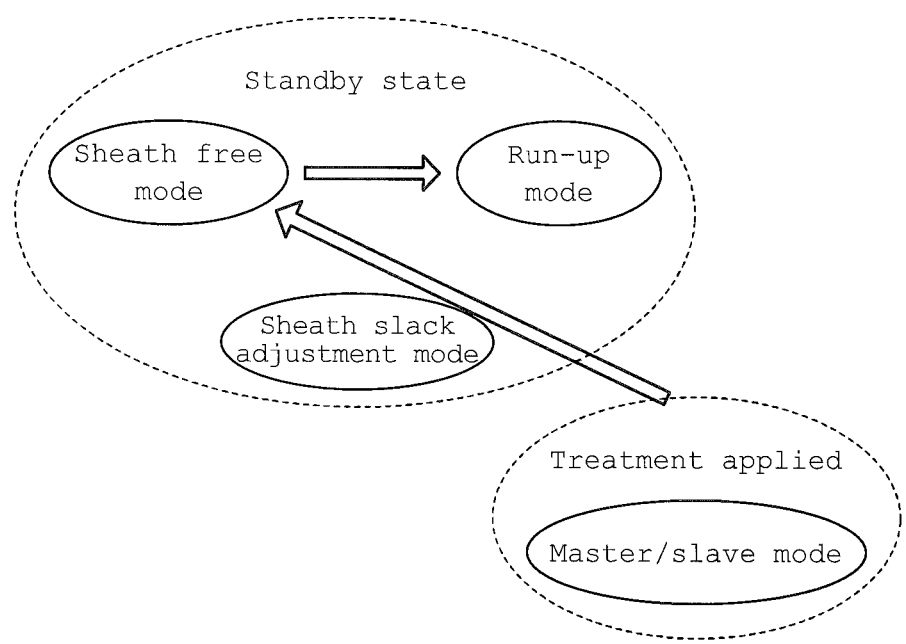
FIG. 14 is indicative of mode transitions to demounting of the insert unit and wire driving unit from the medical instrument according to one embodiment.

FIG. 14 is indicative of the mode transition for disconnection of the insert unit from the wire driving unit in the medical instrument according to the embodiment described herein.

In Step 45 shown in FIG. 11, there is such mode transition as shown typically in FIG. 14. In the master/slave mode, if the connection lock of the insert unit 2 to the wire driving unit 4 being set free is detected, the processing then goes to the sheath free mode. In the sheath free mode, if the disconnection of the insert unit 2 from the wire driving unit 4 is detected, the processing then goes to the run-up mode.

With the medical instrument according to the embodiment described herein, it is thus possible to gain unerring control of the status and mode of the apparatus.

A surgical system 90 is now explained as one example of the medical system to which the medical instrument 1 according to the embodiment described herein is applied.

Figure 15:
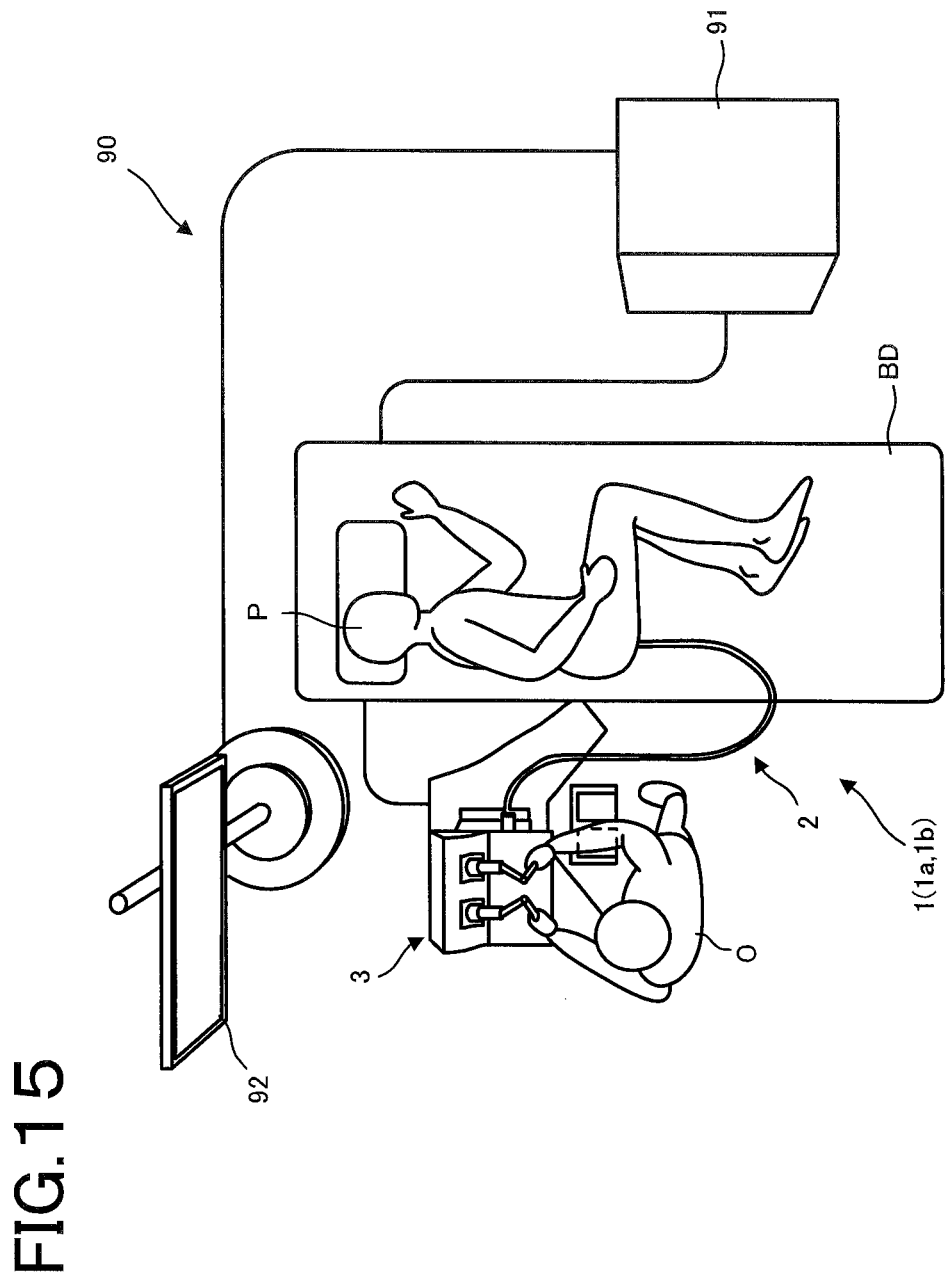
FIG. 15 is illustrative of the surgical system to which the medical instrument according to one embodiment is applied.
Figure 16:
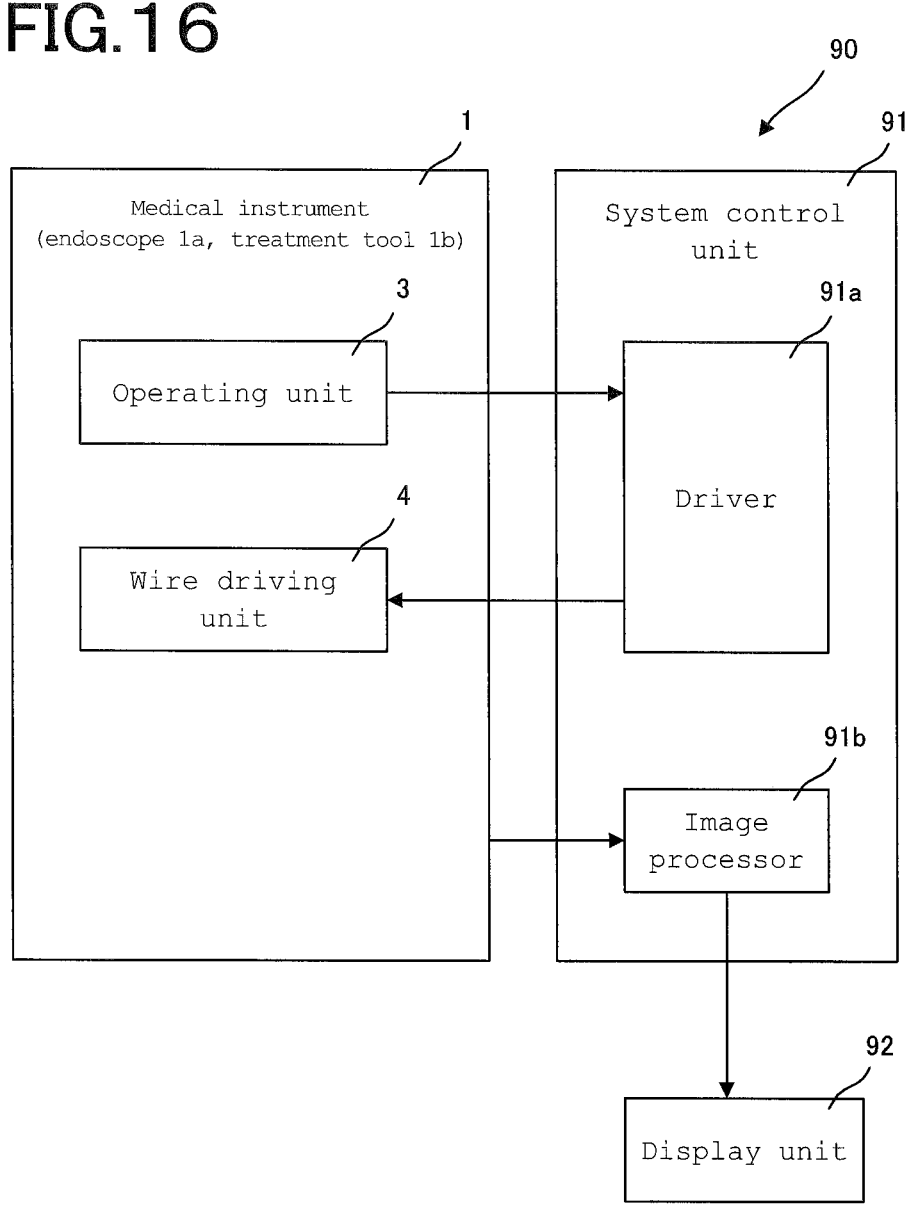
FIG. 16 is illustrative in system architecture of the surgical system to which the medical instrument according to one embodiment is applied.

FIG. 15 is illustrative of a surgical system 90 to which the medical instrument 1 according to the embodiment described herein is applied, and FIG. 16 is illustrative in system architecture of the surgical system 90 to which the medical instrument 1 according to the embodiment described herein is applied.

The medical instrument 1 is applied to the surgical system 90 according to the embodiment described herein. The surgical system 90 includes an operating unit 3 operated by an operator O, a medical instrument 1 such as an endoscope 1*a* having a distal-end insert unit 2 capable of being inserted into the interior of the body of a patent P lying down on an operating table BD, for instance, a soft organic like the large intestine, a system control unit 91 for controlling the medical instrument 1, and a display unit 92 for displaying an image acquired through the medical instrument 1.

The operating unit 3 includes a pair of operating handles attached to an operating table, and a footswitch or the like placed on the floor surface. The operating unit 3 may have a multi-joint structure. The angle of the operating unit 3 in operation is acquired by an angle acquisition unit such as an encoder and in response to the resulting signal, the system control unit 91 puts the wire driving unit 4 into operation by way of a driver 91*a* as shown in FIG. 16.

For instance, the image acquired by the endoscope 5*c* is sent out to an image processor 91*b* within the system control unit 91, and the image processed by the image processor 91*b* is displayed on the display unit 92. Then, the operator O operates the medical instrument 1 while viewing the image appearing on the display unit 92.

According to such surgical system 90, it is possible to display unerring images asked for by the operator O thereby putting the medical instrument 1 into more unerring operation.

It is here noted that the medical instrument 1 used with the surgical system 90 may be such endoscope 1*a* as used in the first embodiment, the treatment tool 1*b* inserted through the endoscope 1*a* as in the second embodiment, or a treatment tool 1*b* separate from the endoscope 1*a*.

As described above, the medical instrument 1 according to one embodiment includes a wire 5, a flexible sheath 6 through which the wire 5 is inserted, a wire driving unit 4 for driving the wire 5, an insert unit 2 that is put into operation as the wire is driven, a sheath pulling driving unit 21 for pulling the sheath 5, a sheath lock unit 20 for locking movement of the sheath pulling driving unit 21, and a control unit 40 for switching among a run-up mode in which the insert unit 2 and the wire driving unit 4 are still disconnected, a sheath free mode in which the sheath 6 is not locked and so set free, a sheath slack adjustment mode in which a slack in the sheath 6 is adjusted to lock the sheath 6 in place and a master/slave mode in which the insert unit 2 connected to the wire driving unit 4 is put into a drivable state. It is thus possible to gain unerring control of the sheath status in association with the status of the apparatus.

The medical instrument 1 according to one embodiment further includes a connection/disconnection detection unit 32 for detection of connection of the insert unit 2 to the wire driving unit 4, a master/slave connection instruction unit 31 for giving an instruction as to the completion of connection of a treatment tool 5 to the wire driving unit 4, a sheath tension measuring unit 33 for measuring a tension of the sheath 6, and a sheath locked-status detection unit 34 for detecting whether or not the sheath 6 is locked in place, wherein the control unit 40 causes a transition to the sheath free mode, when connection of the insert unit 2 to the wire driving unit 4 is detected by the connection/disconnection detection unit 32 in the run-up mode, the control unit 40 causes a transition to the sheath slack adjustment mode, when a signal indicative of the completion of connection of the insert unit 2 to the wire driving unit 4 is entered from the master/slave connection instruction unit 31 in the sheath free mode, and the control unit causes a transition to the master/slave mode, when the sheath 6 is found to have a tension within a given range predetermined by the sheath tension measuring unit 33 and the sheath 6 being locked by the sheath lock unit 13, 20 is detected by the sheath locked-status detection unit 34 in the sheath slack adjustment mode. It is thus possible to make unerring mode transitions from the activation of the apparatus to a mode in which an affected site is treatable.

In the medical instrument 1 according to one embodiment, the control unit 40 causes a transition to the run-up mode, when a signal indicative of the insert unit 2 being still disconnected from the wire driving unit 4 is entered from the connection/disconnection detection unit 32 in the sheath free mode. It is thus possible to gain unerring control of the medical instrument 1 in such a way as not to apply treatment in a state where the insert unit 2 is still disconnected from the wire driving unit 4.

The medical instrument 1 according to one embodiment further includes a sheath pulled-status detection unit 35 for detecting a driving status of the sheath pulling driving unit 21 for pulling the sheath 6, wherein the control unit 40 causes a transition to the sheath free mode, when the sheath 6 is found to have a sheath tension outside a given range predetermined by the sheath tension measuring unit 33 and a driving status of the sheath pulling driving unit 21 detected by the sheath-pulled status detection unit 35 is determined as reaching the limits in the sheath slack adjustment mode. It is thus possible to make unerring slack adjustment in association with the status of the sheath 6.

In the medical instrument 1 according to one embodiment, the control unit 40 causes a transition to the sheath slack adjustment mode, when the sheath 6 is found to have a tension outside a given range predetermined by the sheath tension measuring unit 33 in the master/slave mode. It is thus possible to adjust the slack in the sheath 6 when the status of the sheath 6 is not unerring, thereby using the treatment tool in an unerring state of the sheath 6.

In the medical instrument 1 according to one embodiment, the control unit 40 causes a transition to the run-up mode, when a signal indicative of the insert unit 2 being still disconnected from the wire driving unit 4 is entered from the connection/disconnection detection unit 32 in the master/slave mode. It is thus possible to gain unerring control of the status and mode of the apparatus.

According to one embodiment, there is a medical system 90 provided, wherein the medical instrument 1 is an endoscope 1a including a viewing optical system, an imaging device and a lighting optical system, and the insert unit 2 is defined by a distal-end portion of the endoscope 1a to which one end of the wire 5 is attached and a flexible portion 2c through which the wire 5 and the sheath 6 are inserted, the medical system further includes an operating unit 3 for driving the wire driving unit 4, to which the other end of the wire 5 is attached, to put the distal-end portion 2a and the flexible portion 2c into operation, a display unit 92 for displaying an image acquired through the endoscope 1a, and a system control unit 91 for putting the operating unit 3 into operation thereby controlling the endoscope 1a and permitting the image acquired through the endoscope 1a to be displayed on the display unit 92. It is thus possible to permit an unerring image asked for by an operator O to be displayed, thereby enabling the operator O to put the medical instrument 1 in more unerring operation.

According to one embodiment, there is a medical system 90 provided, wherein the medical instrument 1 is defined by a treatment tool 1b for applying treatments to an affected site (a subject of interest), and the insert unit 2 is defined by a distal end 2a of the treatment tool 1b to which one end of the wire 5 is attached and a flexible portion 2c through which the wire 5 and the sheath 6 are inserted, the medical system 90 further includes an operating unit 3 for driving a wire driving unit 4, to which the other end of the wire 5 is attached, to put the distal end 2a and the flexible portion 2c into operation, an endoscope 1a including a viewing optical system, an imaging device and a lighting optical system, a display unit 92 for displaying an image acquired through the endoscope 1a, and a system control unit 91 for putting the operating unit 3 in operation thereby controlling the endoscope 1a and permitting the image acquired through the endoscope 1a to be displayed on the display unit 92. It is thus possible to permit an unerring image asked for by an operator O to be displayed, thereby enabling the operator O to put the medical instrument 1 into more unerring operation. It is also possible to display endoscopic images concurrently with the status of the treatment tool thereby improving on the operability of the medical instrument 1.

In the medical system 90 according to one embodiment, the treatment tool 1b is inserted through the endoscope 1a. It is thus possible to display the state of the affected site on the eye level of the treatment tool thereby improving on the operability of the medical instrument 1.

One embodiment provides a mode transition method for a medical instrument 1 which includes a wire 5, a flexible sheath 6 through which the wire 5 is inserted, a wire driving unit 4 for driving the wire 5, an passive unit 2 that is put into operation as the wire 5 is driven, a sheath pulling driving unit 21 for pulling the sheath 6, and a sheath lock unit 20 for locking movement of the sheath 6 in place, the method includes a run-up mode in which the insert unit 2 and the wire driving unit 4 are still disconnected, a sheath free mode in which the sheath 6 is not locked and so set free, a sheath slack adjustment mode in which a slack in the sheath 6 is adjusted to lock the sheath 6 in place and a master/slave mode in which the insert unit 2 connected to the wire driving unit 4 is put into an enabling state, the method includes step of:

transiting to the sheath free mode, when the insert unit 2 is connected to the wire driving unit 4 in the run-up mode, transiting to the sheath slack adjustment mode, when completion of connection of the insert unit 2 to the wire driving unit 4 is verified in the sheath free mode, and transiting to the master/slave mode, when the sheath 6 has a sheath tension within a predetermined range and is locked in the sheath slack adjustment mode. It is thus possible to make unerring mode transitions from the activation of the apparatus to a mode in which an affected site is treatable.

One embodiment provides the mode transition method for the medical instrument 1, wherein the step of transiting to the run-up mode is executed, when the insert unit 2 and the wire driving unit 4 are still disconnected in the sheath free mode. It is thus possible to gain unerring control of the medical instrument 1 in such a way as not to apply treatments in a state where the insert unit 2 and the wire driving unit 4 are still disconnected.

One embodiment provides a mode transition method for a medical instrument 1, wherein the step of transiting to the sheath free mode is executed, when the sheath 6 has a tension outside the predetermined range and a driving status of the sheath pulling driving unit 21 is determined as reaching the limits in the sheath slack adjustment mode. It is thus possible to make unerring slack adjustment in association with the status of the sheath 6.

One embodiment provides the mode transition method for the medical instrument 1, wherein the step of transiting to the sheath slack adjustment mode is executed, when the sheath 6 has a tension greater than the predetermined range in the master/slave mode. It is thus possible to adjust the slack in the sheath 6 when the status of the sheath 6 is not unerring, thereby using the treatment tool in an unerring state of the sheath 6.

One embodiment provides the mode transition method for the medical instrument 1, wherein the step of transiting to the run-up mode is executed, when the insert unit 2 is still disconnected from the wire driving unit 4 in the master/slave mode. It is thus possible to gain unerring control of the status and mode of the apparatus.

While the embodiments as described above have been explained with the use of the sheath support member 15, it is to be understood that the sheath 6 may be provided with steps to support the sheath 6 or just only friction may be used to support the sheath 6, dispensing with the sheath support member 15. The wire 5 may be formed of a wire member such as a single wire, a stranded wire, a knitted wire, and so on.

It is here to be appreciated that the invention is in no sense limited to such embodiments as described above. While the explanation of some embodiments embraces numerous specific details for illustration, it would be obvious to those skilled in the art that diverse variations or modifications made thereto are included within the scope of the invention. In other words, illustrative embodiments of the invention are described without excluding generality from the claimed inventions and imposing any limitation thereon.

REFERENCE SIGNS LIST

1: Medical instrument
2: Insert unit (passive unit)
2*a*: Distal-end portion (passive portion)
2*b*: Curving portion (passive portion)
2*c*: Flexible portion (passive portion)
3: Operating unit
4: Wire driving unit
5: Wire
6: Sheath
7: Outer cover
10: Sheath lock mechanism
13: Sheath lock member (sheath lock unit)
15: Sheath support member (sheath pulling unit)
16: Sheath support member guide
18: Through-the-sheath unit
20: Sheath lock driving unit (sheath lock unit)
21: Sheath pulling driving unit (sheath pulling unit)
30: Input block
31: Master/slave connection button
32: Connection/disconnection detection unit for the insert unit (or the passive unit)
33: Sheath tension measuring unit
34: Sheath locked-status detection unit
35: Sheath pulled-status detection unit
36: Wire driving-amount detection unit
37: Mode input unit
40: Control unit
50: Output block
51: Warning unit
52: Mode display unit
90: Surgical system (medical system)
91: System control unit
92: Display unit

The invention claimed is:

1. A medical instrument comprising:
a wire;
a flexible sheath through which the wire is inserted;
a driver for driving the wire;
a passive unit that is put into operation as the wire is driven;
a first actuator for pulling the sheath;
a second actuator for locking movement of the sheath; and
a controller comprising hardware, the controller being configured to switch from one mode to another mode among a run-up mode in which the passive unit and the driver are disconnected, a sheath free mode in which the sheath is not locked so as to move freely, a sheath slack adjustment mode in which a slack in the sheath is adjusted to lock the sheath in place and a master/slave mode in which the passive unit is connected to the driver to put the passive unit into a drivable state.

2. A medical instrument according to claim 1, further comprising:
a first sensor for detection of connection of the passive unit to the driver;
a second sensor for measuring a tension of the sheath; and
a third sensor for detecting whether or not the sheath is locked in place,
wherein the controller is further configured to:
switch to the sheath free mode, when connection of the passive unit to the wire driving unit is detected by the first sensor in the run-up mode,
switch to the sheath slack adjustment mode, when a signal indicative of completion of connection of the passive unit to the driver is received from the first sensor in the sheath free mode, and
switch to the master/slave mode, when the sheath is found to have a tension within a given range predetermined by the second sensor and the sheath being locked by the second actuator is detected by the third sensor in the sheath slack adjustment mode.

3. A medical instrument according to claim 2, wherein the controller is further configured to switch to the run-up mode, when a signal indicative of the passive unit being disconnected from the wire driving unit is received from the first sensor in the sheath free mode.

4. A medical instrument according to claim 2, further comprising a fourth sensor for detecting a driving status of the pulling unit for pulling the sheath,
wherein the controller is further configured to switch to the sheath free mode, when the sheath is found to have a sheath tension outside a given range predetermined by the second sensor and a driving status of the sheath pulling unit detected by the fourth sensor is determined as reaching a predetermined limit in the sheath slack adjustment mode.

5. A medical instrument according to claim 2, wherein the controller is further configured to switch to the sheath slack adjustment mode, when the sheath is found to have a tension outside a predetermined range by the second sensor in the master/slave mode.

6. A medical instrument according to claim 2, wherein the controller is further configured to switch to the run-up mode, when a signal indicative of the passive unit being disconnected from the driver is received from the first sensor in the master/slave mode.

7. A medical system comprising:
the medical instrument according to claim 1, the medical instrument being an endoscope including a viewing optical system, an imaging device and a lighting optical system, and the passive unit is a distal-end portion of the endoscope to which one end of the wire is attached and a flexible portion through which the wire and the sheath are inserted,
a operation section for driving the driver, to which an other end of the wire is attached, to put the distal-end portion and the flexible portion into operation,
a display for displaying an image acquired through the endoscope, and
a system controller comprising hardware, the system controller being configured to put the operation section into operation to control the endoscope and permit the image acquired through the endoscope to be displayed on the display.

8. A medical system comprising:
the medical instrument according to claim 1, the medical instrument being a treatment tool configured to apply treatment to a subject, and the passive unit is a distal end of the treatment tool to which one end of the wire is attached and a flexible portion through which the wire and the sheath are inserted,
an operation section for driving the driver, to which an other end of the wire is attached, to put the distal end and the flexible portion into operation,
an endoscope including a viewing optical system, an imaging device and a lighting optical system,
a display for displaying an image acquired through the endoscope, and
a system controller comprising hardware, the system controller being configured to put the operation section into operation to control the treatment tool and permit the image acquired through the endoscope to be displayed on the display.

9. A medical system according to claim 8, wherein the treatment tool is inserted through the endoscope.

10. A mode transition method for use with a medical apparatus, wherein the medical apparatus comprising a wire, a flexible sheath through which the wire is inserted, a driver for driving the wire, a passive unit that is put into operation as the wire is driven, a first actuator for pulling the sheath, and a second actuator for locking movement of the sheath, the medical apparatus being configured to switch from one mode to another mode among a run-up mode in which the passive unit and the driver are disconnected, a sheath free mode in which the sheath is not locked so as to move freely, a sheath slack adjustment mode in which a slack in the sheath is adjusted to lock the sheath in place, and a master/slave mode in which the passive unit connected to the driver is put into an enabling state, the method comprising:
switching to the sheath free mode, when the passive unit is connected to the driver in the run-up mode;
switching to the sheath slack adjustment mode, when completion of connection of the passive unit to the driver is verified in the sheath free mode; and
switching to the master/slave mode, when the sheath has a sheath tension within a predetermined range and is locked in the sheath slack adjustment mode.

11. The mode transition method for medical apparatus according to claim 10, wherein the switching to the run-up mode is executed when the passive unit is disconnected from the driver in the sheath free mode.

12. The mode transition method for medical apparatus according to claim 10, wherein the switching to the sheath free mode is executed when the sheath has a tension outside the predetermined range and a driving status of the first actuator is determined as reaching a predetermined limit in the sheath slack adjustment mode.

13. The mode transition method for medical apparatus according to claim 10, wherein the switching to the sheath slack adjustment mode is executed when the sheath has a tension outside the predetermined range in the master/slave mode.

14. The mode transition method for medical apparatus according to claim 10, wherein the switching to the run-up mode is executed when the passive unit is disconnected from the wire driving unit in the master/slave mode.

* * * * *